US00PP11582P

United States Patent [19]

Lemon

[11] Patent Number: Plant 11,582

[45] Date of Patent: Oct. 17, 2000

[54] REGAL PELARGONIUM PLANT NAMED 'BRILLIANCE'

[75] Inventor: David G. Lemon, Lompoc, Calif.

[73] Assignee: Oglevee, Ltd.

[21] Appl. No.: 09/162,686

[22] Filed: Sep. 29, 1998

[51] Int. Cl.[7] ..... A01H 5/00

[52] U.S. Cl. ..... Plt./331

[58] Field of Search ..... Plt./331

[56] References Cited

U.S. PATENT DOCUMENTS

P.P. 6,027 9/1987 Kirmann ..... Plt./331

P.P. 10,024 9/1997 Lemon ..... Plt./331

*Primary Examiner*—Howard J. Locker

*Assistant Examiner*—Wendy A Baker

*Attorney, Agent, or Firm*—Webb Ziesenheim Logsdon Orkin & Hanson, P.C.

[57] ABSTRACT

A new and distinct regal geranium plant with a crisp white flower having a medium lavender eye above medium green foliage. The new variety has a controlled growth habit and has more florets and a shorter flowering time and is more reliable than 'Jennifer'.

1 Drawing Sheet

BACKGROUND OF THE INVENTION

This discovery relates to a new and distinct variety of geranium plant identified by the varietal name of 'Brilliance', Breeder No. 4DG649 and Oglevee, Ltd. No. 99. The new variety was discovered by David G. Lemon in a selected breeding program at Oglevee, Ltd. in Connellsville, Pa. The new variety is a selection from the crossing of a breeding variety, Oglevee, Ltd. No. 261 (unpatented), and the commercial variety 'Mary', U.S. Plant Pat. No. 6,027. It was first asexually reproduced by cuttings on Aug. 14, 1995 at Connellsville, Pa. and has been found to retain its distinctive characteristics through successive propagations.

The new variety, when grown in a glass greenhouse in Connellsville, Pa. using full light, 60° F. night temperature, 68° F. day temperature and grown in a soilless media with constant fertilizer at 150–200 ppm nitrogen and potassium, has a response time from a rooted cutting to a flowering plant in a 6 inch pot of fourteen weeks. Rooted cuttings potted on Oct. 15, 1997 flowered on Feb. 9, 1998.

DESCRIPTION OF THE DRAWING

The accompanying photographic drawing illustrates the new variety, with the color being as nearly true as is possible with color illustrations of this type.

DESCRIPTION OF THE PLANT

The following detailed descriptions set forth the characteristics of the new variety. The data which define these characteristics were collected from asexual reproductions carried out at Oglevee, Ltd., 152 Oglevee Lane, Connellsville, Pa. 15425. The color readings on a plant grown in a 5 inch pot were taken indoors under 200–220 foot candles of cool white fluorescent light. Color references are primarily to the R.H.S. Colour Chart of The Royal Horticultural Society of London.

THE PLANT

Classification:

*Botanical.*—*Pelargonium×domesticum.*

*Commercial.*—Regal geranium named 'Brilliance'.

Form: Upright medium mound.

Height: 21–23 cm above top of pot.

Growth: Medium plant habit with free basal branching.

Strength: Does not require artificial support.

Foliage: Stalked leaf attachment; slightly reflective.

Leaves:

*Size.*—8.0–13.0 cm across.

*Shape.*—Reniform; truncate base.

*Margin.*—Serrately lobed.

*Texture.*—Leathery, pubescent.

*Color.*—Top: Green Group 137A. Bottom: Green Group 137D. Zone: None.

*Ribs and veins.*—Venation: Palmate. Color: Green Group 143D.

Petioles:

*Length.*—4.0–4.5 cm.

*Color.*—Green Group 143C.

Stem:

*Color.*—Yellow-Green Group 144A.

*Internode length.*—2.0–3.0 cm.

THE BUD

Shape:

*Overall.*—Elliptical cluster when just showing color.

*Individual buds.*—Elliptical or oval when just showing color.

Size: 3.5–5.0 cm across.

INFLORESCENCE

Blooming habit: Continuous flowering; large florets forming a full flower head.

Borne: Umbel of 6 to 12 florets, florets on pedicel, pedicel on peduncle at 4.0–5.0 cm above foliage.

Closed florets:

*Bud size.*—2.0–2.5 cm long.

Open florets:

*Form.*—Slightly cupped.

*Size of fully open bloom.*—Umbels: 11.0–12.5 cm across. Florets: 3.2–5.0 cm wide; 4.5–5.0 cm long.

*Color.*—Top: White Group 155D. Bottom: White Group 155D with a pale eye of Purple Group 78D showing through. Eye: Two petals have an eye of Red-Purple Group 70B and veining of Purple Group 78A; one petal has slight veining of Red-Purple Group 70B.

*Petals*.—5–6 in number.

Texture and appearance: Satiny, highly reflective; appears from a distance as a crisp white bloom with a medium lavender eye above medium green foliage.

Petaloids: None.

Pedicel:

*Length*.—2.4–3.0 cm.

*Color*.—Yellow-Green Group 144A with Green Group 137A toward flower.

Peduncle:

*Length*.—6.0–8.5 cm.

*Color*.—Yellow-Green Group 144A with some Greyed-Purple Group 183A shading.

Disease resistance: No unusual susceptibility to diseases of Pelargonium has been observed.

Lasting quality: Continuous blooming; slow to shatter; overall plant bloom holds up 14–21 days when brought into the home.

REPRODUCTIVE ORGANS

Stamens:

*Anthers*.—4.0 mm long.

*Filaments*.—1.5–2.0 cm long; white in color.

*Pollen color*.—Golden orange.

Pistils:

*Number*.—1.

*Length*.—2.6–2.8 cm.

*Stigma color*.—Red-Purple Group 71A.

*Style*.—1.2–1.5 cm long.

*Ovaries*.—Pale green in color; pubescent; 1.0 cm long.

Fruit: None observed.

GENERAL CHARACTERISTICS

While cutting production and rooting speed are equal to or better than 'Jennifer' (U.S. Plant Pat. No. 10,024), floret count has increased greatly and flowering time is shorter and more reliable. The plant habit is more controlled as well. The flower on 'Brilliance' is a crisp white with a medium lavender eye, while 'Jennifer' has a clear white flower with no eye. This new variety has been trialed during the winters and springs of 1996 and 1997 and has proven better than 'Jennifer' repeatedly. 'Brilliance' is similar in appearance to its parent cultivar, 'Mary', however 'Brilliance' has a shorter rooting time. 'Mary' may take up to 4 weeks to root while 'Brilliance' develops roots in only 14 days.

I claim:

1. A new and distinct variety of geranium plant named 'Brilliance' as described and illustrated herein.

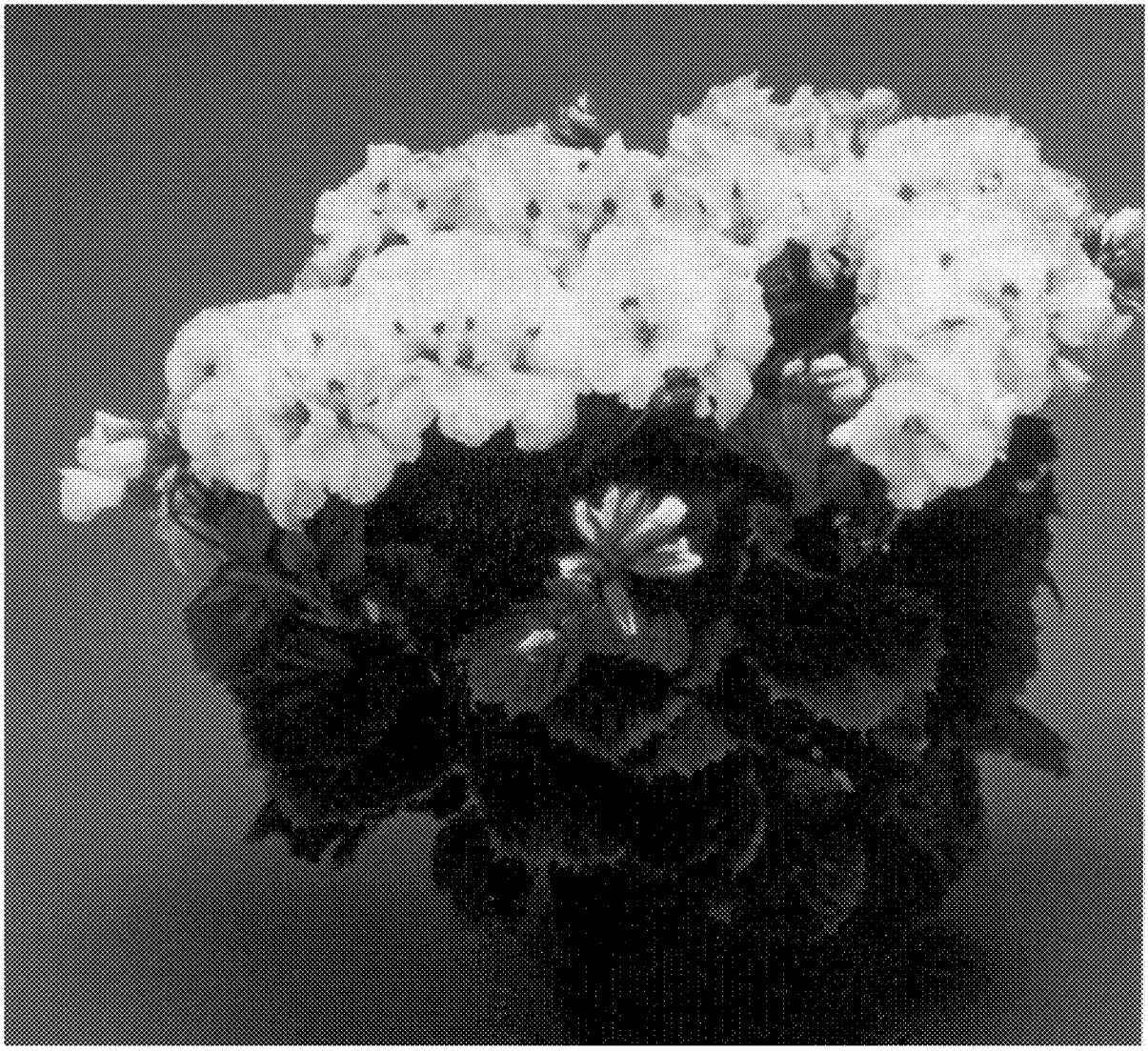

* * * * *